United States Patent [19]

Muller

[11] Patent Number: 4,871,369
[45] Date of Patent: Oct. 3, 1989

[54] LONG STEM HIP IMPLANT

[75] Inventor: Charles J. Muller, Gillette, N.J.

[73] Assignee: Pfizer Hospital Products Group, Inc., New York, N.Y.

[21] Appl. No.: 124,134

[22] Filed: Nov. 23, 1987

[51] Int. Cl.$^4$ ............................................. A61F 2/32
[52] U.S. Cl. ................................................... 623/23
[58] Field of Search ....................... 623/16, 18, 19, 20, 623/22, 23

[56] References Cited

U.S. PATENT DOCUMENTS

| | | | |
|---|---|---|---|
| 3,584,318 | 6/1971 | Scales et al. | 623/18 |
| 3,871,031 | 3/1975 | Boutin | 623/16 |
| 4,101,985 | 7/1978 | Baumann et al. | 623/22 |
| 4,404,691 | 9/1983 | Buning et al. | 623/23 |
| 4,406,023 | 9/1983 | Harris | 623/22 |
| 4,435,854 | 3/1984 | Keller | 623/22 |
| 4,546,501 | 10/1985 | Gustilo et al. | 623/23 |
| 4,551,863 | 11/1985 | Murray | 623/23 |
| 4,578,081 | 3/1986 | Harder | 623/18 |
| 4,589,883 | 5/1986 | Kenna | 623/22 |
| 4,608,053 | 8/1986 | Keller | 623/23 |
| 4,657,551 | 4/1987 | Ecke | 623/23 |
| 4,658,808 | 4/1987 | Link | 623/16 |

FOREIGN PATENT DOCUMENTS

| | | | |
|---|---|---|---|
| 0038908 | 11/1981 | European Pat. Off. | 623/23 |
| 0128036 | 12/1984 | European Pat. Off. | 623/23 |
| 2851598 | 6/1980 | Fed. Rep. of Germany | 623/23 |
| 2854334 | 6/1980 | Fed. Rep. of Germany | 623/23 |
| 2580171 | 10/1986 | France | 623/23 |

OTHER PUBLICATIONS

Zimmer, "Product Brochure", Hip Prosthesis Size Definition Chart, (A-3), Jan. 1974.

Primary Examiner—Richard J. Apley
Assistant Examiner—David J. Isabella
Attorney, Agent, or Firm—Peter C. Richardson; Lawrence C. Akers; Elizabeth O. Slade

[57] ABSTRACT

A femoral hip implant for use in patients requiring a long distal section of the femoral component is provided. For example, it can be used in patients undergoing revision surgery or requiring an implant with a long stem because of a fracture in the femur or a bone defect (for example as a result of a tumor removal). The implant is specially curved in its distal section so that the implant avoids impingement on the wall of the medullary canal even in the region of the isthumus of the bone.

8 Claims, 2 Drawing Sheets

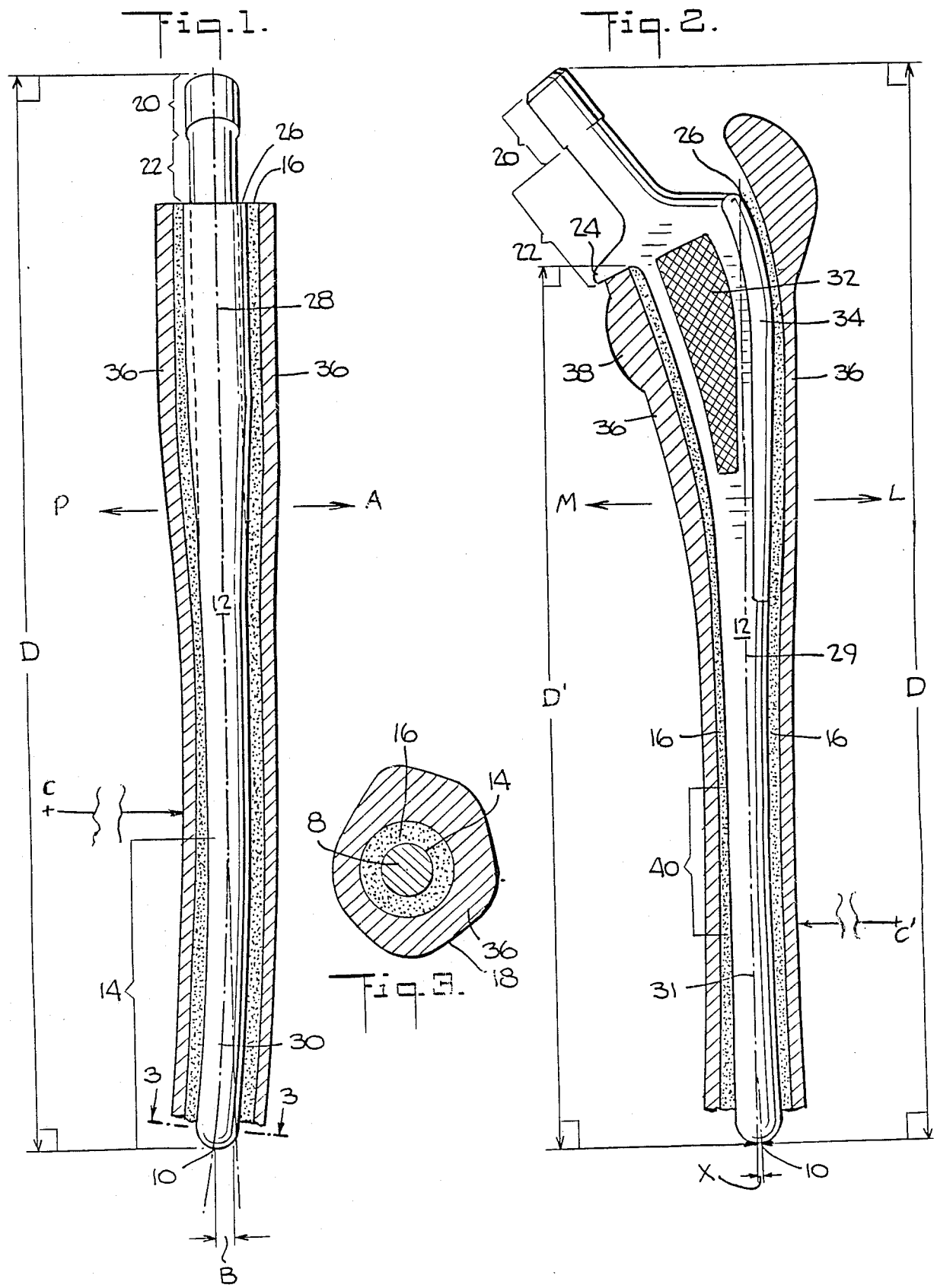

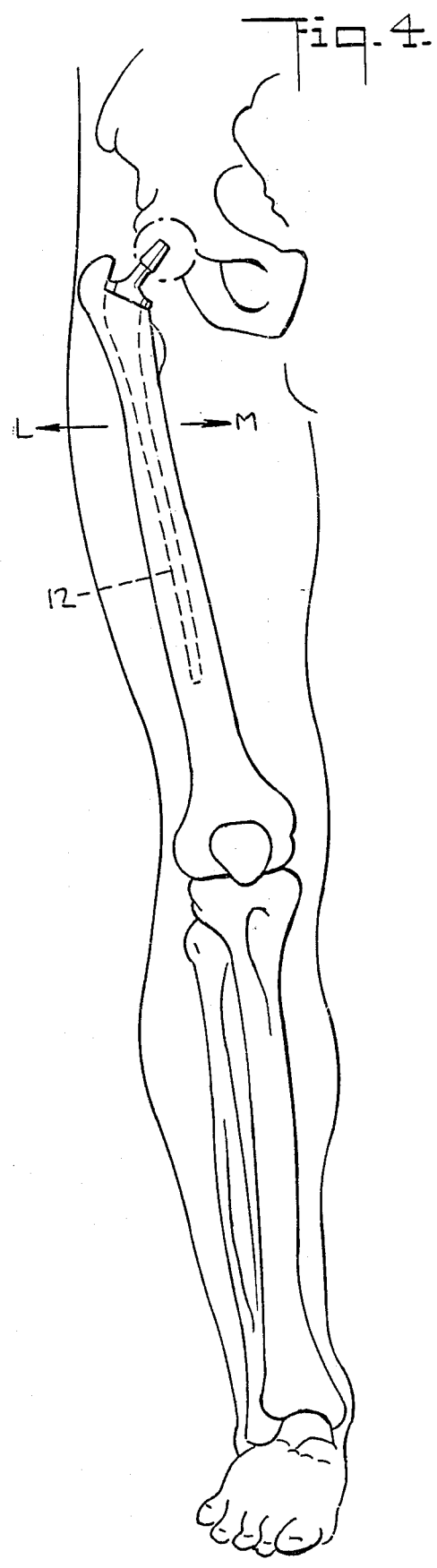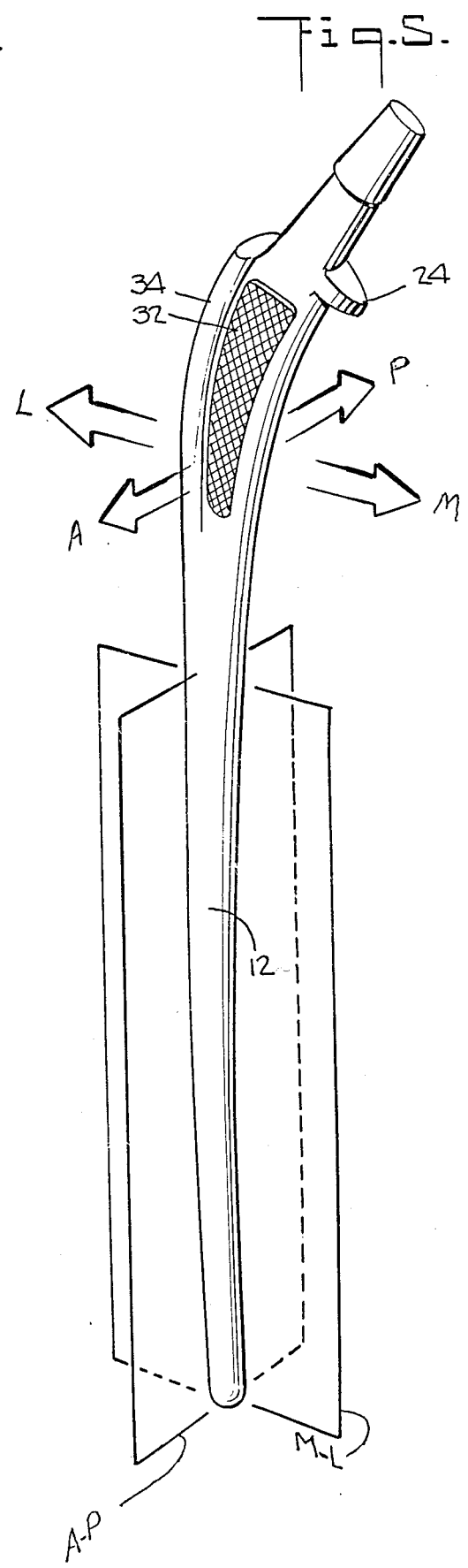

LONG STEM HIP IMPLANT

BACKGROUND OF THE INVENTION

For operations involving patients who require multiple hip surgeries, it is often necessary to replace a femoral hip implant with a long stem hip implant. That is, a short stem hip implant is not generally used for revisions. Long stem hip implants can also be used in other situations. For example, they can be used in patients undergoing revision surgery or requiring an implant with a long stem because of a fracture in the femur or a bone defect (for example as a result of tumor removal).

However, when such a long stem hip implant is fully implanted, it is very important that its distal end be centered in the medullary canal. If the distal end is not centered, a non-uniform cement mantle will result as the implant is inserted into the canal containing cement. Then, unequal stresses on the cement mantle may result in failure of the cement mantle. Such failure can eventually result in loosening of the implant.

Additionally, because long stem hip prostheses generally extend in the femur beyond the region referred to as the isthumus of the femur (where the cortical bone thickens and the opening in the intramedullary canal decreases), correct placement of a long stem prosthesis presents a special challenge to the physician.

Broaches are often used to prepare the medullary canal. These broaches can be designed to rotate slightly into anteversion (i.e., the neck of the broach rotates forward as the broach is driven into the bone). The final orientation mimics the natural anatomic orientation of the femoral neck. This rotation (which is approximately 10°) presents no problem in the alignment of a short prosthesis, wherein the stem is not long enough to impinge on the curved section of the femur, particularly in the region of the isthmus. However, when a long, bowed stem is used as a prosthesis, the rotation will often result in poor placement of the distal tip of the implant.

It is known in the prior art to have "anatomically" shaped prostheses which have been made with simple distal bows and/or distal and proximal curvatures. However, the distal tip of the implant must still be correctly positioned, as described above. The problem of positioning an implant within the isthmus of the bone has not previously been adequately addressed in the prior art.

Additionally, for economic purposes, it is desirable to have a limited number of ready-made long stem hip implants for use by the population requiring such implants.

OBJECTS OF THE INVENTION

An object of this invention is to provide a femoral component suitable for use in patients having hip surgery requiring a long stem prosthesis.

Another object of this invention is a long stem hip implant which is suitable for a large segment of the population requiring revision surgery.

Yet another object of this invention is a modular long stem hip implant.

These and other objects are satisfied by the invention described and claimed herein.

SUMMARY OF THE INVENTION

According to the invention a hip joint prosthetic device (which is suitable for use in a large segment of the population requiring revision surgery, without modification of that device) comprises a femoral component having a long stem which is sufficiently long when implanted so that it extends beyond the isthmus in the femur, which is substantially straight over its major extent, but which is curved in a very particular way, described below, in the distal section of the stem. That curve in the distal section of the stem is formed generally from two components.

The stem of the invention can be viewed as having a single curve, which has a component in the A-P (anterior/posterior) plane and another component in the M-L (medial-lateral) plane. That is, the projection of this single curve on the A-P plane and the projection of the single curve on the M-L plane can be discussed as two curves, even though the femoral component stem actually includes only one curve in three-dimensional space in its distal section. The components of the curve will be discussed separately herein. The first and the second of these components are two curves located in perpendicular planes. One of these components is a curve lying in the A-P plane and is the projection of the single curve on the A-P plane. The A-P component is a simple curve having its center of curvature (when positioned in the body) posterior to the axis of the femur. The second component of the single curve is the projection of the single curve on the M-L plane, which also is a simple curve but its center of curvature is lateral to the axis of the femur. The stem of the resulting device avoids impingement on the wall of the medullary canal, even in the region of the isthmus.

Also, according to the invention, the distal portion of the long stem femoral hip implant may be used as a component of a modular device.

BRIEF DESCRIPTION OF THE DRAWINGS

FIG. 1 is a plan view of an embodiment of the device of the invention, for use in a right femur as viewed in the A-P plane from the lateral direction. A portion of a right femur is shown with cross-hatching.

FIG. 2 is a plan view of the device of FIG. 1 as viewed in the M-L plane from the dorsal direction. A portion of a right femur is shown with cross-hatching.

FIG. 3 is a cross-sectional view of the device of FIG. 1, as viewed near its distal end, taken along line 3—3 in FIG. 1, and located within the medullary canal, showing cement surrounding the device.

FIG. 4 is a schematic illustration of a right human leg, showing the device of FIG. 1 in dotted lines, located within a right femur.

FIG. 5 is a pictorial representation of the device of FIG. 1, showing its relationship with respect to the M-L plane and the A-P plane at a time when the device has just been inserted into the body and prior to its being rotated about 10° by the physician.

DESCRIPTION OF THE PREFERRED EMBODIMENTS

Referring to FIGS. 1, 2, and 5, there is shown the long stem hip implant of the present invention implanted in the right femur. For purposes of description arrow "A" indicates the anterior direction with respect to the body, "P" the posterior direction, "M" the medial and "L" the lateral direction.

As shown in FIGS. 1 and 2 each of the components of the curve in the stem of the hip implant 12 of the invention is a simple curve having one center of curvature. (This is in contradistinction to a compound curve.)

The curve component lying in the A-P plane shown in FIG. 1 has a center of curvature C which is indicated as being at a broken distance from the curved component of implant 12 due to drawing space considerations which is posterior to the axis of the femur and to the axis of the stem when the device is positioned in the body.

The curve component lying in the M-L plane shown in FIG. 2 has a center of curvature C (which is indicated as being at a broken distance from the curved component of implant 12 due to drawing space considerations) lateral to the axis of the femur and to the axis of the stem when the device is positioned in the body.

As shown in FIGS. 1 and 2, the component of curvature lying in the A-P plane is the larger and more visually obvious of the two curve components. That is, distance B in FIG. 1 is substantially larger than distance X in FIG. 2, which reflects a substantially smaller average radius of curvature in the A-P plane than in the M-L plane. The bend positions the distal tip 10 of the prosthesis posteriorly with respect to the body, thus accommodating the natural curve of the mid-shaft of the femur and avoiding impingement of the prosthesis on the canal even in the region of the isthmus.

The curve component in the M-L plane is less pronounced, begins more distally on the stem (as compared with the curve in the A-P plane, described above), and positions the tip 10 of the prosthesis 12 laterally with respect to the body (see FIG. 2).

As shown in FIG. 3, this curve in the stem of the prosthesis 12 of the invention helps to keep the distal section 14 of the stem centered in the cement 16 in the medullary canal of the femur 18.

Also shown in FIGS. 1 and 2 are other features and parts of the device of the invention. These include the trunion 20, onto which a head component (not shown) can be attached. The neck 22 connects the trunion 20 to the collar 24 (shown only in FIG. 2). The lateral aspect 26 of the proximal portion of the stem is shown. The centerline 28 of the proximal portion of stem 12 in the A-P plane is shown in FIG. 1 to be coplanar with the centerline of the neck 22, and no anteversion of the neck with respect to the proximal stem is present.

The centerline 30 in the A-P plane and the centerline 31 in the M-L plane of the distal portion of the stem are curved.

B is the perpendicular distance in the A-P plane between the centerline 30 at the distal tip 10 of the implant and the extension in space of the centerline 28 in the A-P plane of the proximal portion of stem 12. X is the perpendicular distance in the M-L plane between the centerline 31 at the distal tip 10 of the implant and the extension in space of the centerline 29 in the M-L plane of the proximal portion of stem 12. Suitable values for X and B (defined above) are shown in the table below for the stem lengths provided. For the primary (i.e., the more prominent) curve in every case, the radius of curvature for C is 1140 mm. For the secondary (i.e., the less prominent) curve, the radius of curvature for C' varies, as shown in the table under the heading r(mm).

In FIG. 2, one can see the textured surface 32 which improves cement adhesion to the device. The lateral flare 34 improves the stress distribution in the bone cement mantle. The thickness of bone 36 is crosshatched in the FIGS. 1, 2, and 3. The cement 16 is shown with a dotted area in the figures.

Regions of bone 36 are indicated, including the lesser trochanter 38 and the region of the isthmus 40 of the femur.

The stem length of the long stem hip implant of this invention will be sufficiently long for a given patient so that the distal tip of the implant extends beyond the isthmus in the intramedullary canal of the patient's femur. The length of the stem D will therefore generally be at least about 200 mm.

It has been found that four sizes of the proximal section of the femoral component of the long stem prosthesis of the invention with two lengths of each size will fit most femora encountered in patients requiring hip surgery. For these, the distance D in FIG. 1 and FIG. 2 will be within the range from about 21 to about 35 cm in length.

The stem lengths of these four sizes of long stem hip implants are given in the following table, with two stem lengths for each size. Also given is a range of suitable associated neck lengths for these four sizes. It is noted that the use of different heads will provide different effective neck lengths contributing to the total length of the implant.

TABLE

| Size | Stem length D' (mm) | Neck length (mm) | B (mm) | X (mm) | r (mm) |
| --- | --- | --- | --- | --- | --- |
| 1 | 175/225 | 36 | 9.0 | 0,20 | 1900 |
| 2 | 200/250 | 41 | 9.0 | 1.6 | 2600 |
| 3 | 225/275 | 44 | 11.9 | 2.0 | 3300 |
| 4 | 225/300 | 46 | 15.0 | 4.0 | 2700 |

In prior art long stem bowed prostheses, the plane of the bow is perpendicular to the plane of the proximal stem. Anteversion, if present at all, is accomplished by a rotation of the neck of the device itself with respect to the long axis of the stem. That is, the centerline of the neck is not coplanar with the centerline of the proximal stem.

The device of this invention having the centerline of its neck preferably coplanar with the centerline of the proximal stem allows anteversion of the proximal stem by the physician without risking impingement of the distal stem on the intramedullary canal.

The devices of the invention are implanted into the body by the following general procedure. A soft tissue dissection is made to expose the joint capsule. The femoral head is then dislocated from the acetabulum and the femoral head is removed (or the old prosthesis is removed if revision surgery is being done). The medullary canal is either reamed and broached (or the old cement is removed if revision surgery is being done). Then cement is injected into the canal and the prosthesis is inserted. The entire implant is then rotated forward preferably about 10° to 12° with respect to the M-L plane during the implanting procedure. This rotation accomplishes the anteversion, and there is preferably no anteversion of the neck of the prosthesis with respect to its shank.

It is noted that in the device of the invention, the curved portion is preferably located only in the distal section 14 of the stem. However, minor, insignificant curves in other sections of the device could also be present, and such a device would fall within the scope of this invention, provided that the curves in the distal segment (described above) are present.

When made of metal, the devices of the invention can be produced so that initially they have no curvature. The two components of the curves can be made in two separate bending operations. Alternatively, the stem can be forged in a single operation to its final configuration.

Preferably, the long stem femoral components are forged to the final configuration. The trunion for the head is machined and ground, and the forging flash is removed by hand-finishing operations.

Although it is expected that the devices of the invention will usually be made of metal, any biocompatible material can be used, so long as the final product has the configuration described above and has sufficient strength and other required properties for a prosthetic hip implant.

A long stem femoral component of the invention can be used as part of a modular system if desired.

I claim:

1. A long stem hip join prosthetic device for implantation into the reamed or broached out medullary canal of the femur comprising:

a femoral component having an intramedullary stem having a proximal and a distal portion the combined length of which, when implanted, is longer than the distance in the intramedullary canal from the femur lesser trochanter to the isthmus, said proximal portion of said intramedullary stem being substantially over its major extent, said distal portion made up of a first component and a second component, wherein (a) said first component is the projection of said distal curve on the A-P plane and is a simple curve having its center of curvature (when positioned in the body upon implantation) lying posteriorly with respect to the axis of the femur; and (b) said second component is the projection of said distal curve on the M-L plane and is a simple curve having its center of curvature (when positioned in the body upon implantation) lying laterally with respect to the axis of the femur, said curvature of said second component beginning at a point closer to a tip of said distal portion than the curvature of said first component.

2. A device according to claim 1, wherein said first component lying in the A-P plane has a smaller radius of curvature than the curve component lying in the M-L plane.

3. A device according to claim 1, wherein said femoral component includes a neck having a centerline coplanar with a centerline of said proximal portion.

4. A device according to claim 3 wherein the length of said stem is at least about 200 mm.

5. A device according to claim 1, wherein, the curvature of said second curve component and the curvature of said first curve component have predetermined radii resulting in a stem which avoids impingement on the wall of the medullary canal when the prosthetic device is inserted and rotated therein at an angle from about 10° to about 12° with respect to the M-L plane.

6. A device according to claim claim 1 wherein the distal section and the proximal section of said device are separable from each other.

7. A device according to claim 1, wherein said intramedullary stem has a cross-section relative to the cross-section of the reamed out or broached out medullary canal producing a predetermined concentric gap therebetween such that the device is spaced from the wall of said medullary canal.

8. A device according to claim 1 wherein said femoral component includes a neck having a centerline in a plane parallel to a plane containing the centerline of said proximal portion so that all anteversion is accomplished by the procedure of rotating said prosthesis with respect to the M-L plane during its insertion into the medullary canal of the patient.

* * * * *